(12) United States Patent
Swanstrom et al.

(10) Patent No.: US 7,520,884 B2
(45) Date of Patent: Apr. 21, 2009

(54) METHODS FOR PERFORMING GASTROPLASTY

(75) Inventors: Lee L. Swanstrom, Portland, OR (US); Richard C. Ewers, Fullerton, CA (US); Tracy D. Maahs, Rancho Santa Margarita, CA (US); Eugene G. Chen, Carlsbad, CA (US); Vahid Saadat, Atherton, CA (US)

(73) Assignee: USGI Medical Inc., San Clemente, CA (US)

( * ) Notice: Subject to any disclaimer, the term of this patent is extended or adjusted under 35 U.S.C. 154(b) by 341 days.

(21) Appl. No.: 10/841,233

(22) Filed: May 7, 2004

(65) Prior Publication Data

US 2005/0250980 A1    Nov. 10, 2005

(51) Int. Cl.
*A61B 17/08* (2006.01)
(52) U.S. Cl. ..................................................... 606/153
(58) Field of Classification Search ............... 623/23.65; 600/29, 30, 37, 104, 106; 128/898; 606/153
See application file for complete search history.

(56) References Cited

U.S. PATENT DOCUMENTS

| | | | |
|---|---|---|---|
| 3,551,987 A | 1/1971 | Wilkinson |
| 4,245,624 A | 1/1981 | Komiya |
| 4,724,840 A | 2/1988 | McVay et al. |
| 4,841,888 A | 6/1989 | Mills et al. |
| 5,037,433 A | 8/1991 | Wilk et al. |
| 5,059,201 A | 10/1991 | Asnis |
| 5,088,979 A | 2/1992 | Filipi et al. |
| 5,222,508 A | 6/1993 | Contarini |
| 5,222,963 A | 6/1993 | Brinkerhoff et al. |
| 5,254,126 A | 10/1993 | Filipi et al. |

(Continued)

FOREIGN PATENT DOCUMENTS

EP    0 480 428 A2    4/1992

(Continued)

OTHER PUBLICATIONS

Chuttani et al., "A Novel Endoscopic Full-thickness Plicator for Treatment of GERD: An Animal Model Study," Gastrointestinal Endoscopy, vol. 26, No. 1,(2002), pp. 116-122.

(Continued)

*Primary Examiner*—William H Matthews
(74) *Attorney, Agent, or Firm*—Levine Bagade Han LLP; Charles C. Fowler (57) ABSTRACT

Methods for performing gastroplasty include reducing the effective volume or cross-sectional area of the stomach via approximation of gastric tissue. Such reduction preferably is achieved endoluminally, either with or without laparoscopic ports. In one variation, a sleeve, pouch, Magenstrasse and Mill, Vertical Banded Gastroplasty ("VBG"), etc.,is formed within the stomach by approximating opposing anterior and posterior segments or ridges of the stomach wall at locations inferior to the gastroesophageal junction. In another variation, opposing walls of the stomach are approximated at a plurality of substantially random locations to reduce an effective volume of the stomach. In yet another variation, both a sleeve and random approximations are formed, the random approximations preferably disposed in a portion of the stomach excluded by the sleeve. In still another variation, opposing walls of the stomach are approximated over significant lengths at random or specified locations.

5 Claims, 6 Drawing Sheets

U.S. PATENT DOCUMENTS

| | | | |
|---|---|---|---|
| 5,327,914 A | 7/1994 | Shlain | |
| 5,345,949 A | 9/1994 | Shlain | |
| 5,374,275 A | 12/1994 | Bradley et al. | |
| 5,382,231 A | 1/1995 | Shlain | |
| 5,395,030 A | 3/1995 | Kuramoto et al. | |
| 5,403,326 A | 4/1995 | Harrison et al. | |
| 5,403,329 A | 4/1995 | Hinchcliffe | |
| 5,431,666 A | 7/1995 | Sauer et al. | |
| 5,433,721 A | 7/1995 | Hooven et al. | |
| 5,462,561 A | 10/1995 | Voda | |
| 5,465,894 A | 11/1995 | Clark et al. | |
| 5,501,691 A | 3/1996 | Goldrath | |
| 5,527,322 A | 6/1996 | Klein et al. | |
| 5,540,704 A | 7/1996 | Gordon et al. | |
| 5,549,621 A | 8/1996 | Bessler et al. | |
| 5,562,686 A | 10/1996 | Sauer et al. | |
| 5,562,688 A | 10/1996 | Riza | |
| 5,571,116 A | 11/1996 | Bolanos et al. | |
| 5,573,540 A | 11/1996 | Yoon | |
| 5,613,974 A | 3/1997 | Andreas et al. | |
| 5,613,975 A | 3/1997 | Christy | |
| 5,626,588 A | 5/1997 | Sauer et al. | |
| 5,632,752 A | 5/1997 | Buelna | |
| 5,662,663 A | 9/1997 | Shallman | |
| 5,700,273 A | 12/1997 | Buelna et al. | |
| 5,749,893 A | 5/1998 | Vidal et al. | |
| 5,779,719 A | 7/1998 | Klein et al. | |
| 5,782,859 A | 7/1998 | Nicholas et al. | |
| 5,787,897 A | 8/1998 | Kieturakis | |
| 5,792,152 A | 8/1998 | Klein et al. | |
| 5,792,153 A | 8/1998 | Swain et al. | |
| 5,810,849 A | 9/1998 | Kontos | |
| 5,817,110 A | 10/1998 | Kronner | |
| 5,836,955 A | 11/1998 | Buelna et al. | |
| 5,860,991 A | 1/1999 | Klein et al. | |
| 5,868,762 A | 2/1999 | Cragg et al. | |
| 5,887,594 A | 3/1999 | LoCicero, III | |
| 5,897,562 A | 4/1999 | Bolanos et al. | |
| 5,901,895 A | 5/1999 | Heaton et al. | |
| 5,928,264 A | 7/1999 | Sugarbaker et al. | |
| 5,947,983 A | 9/1999 | Solar et al. | |
| 5,954,732 A | 9/1999 | Hart et al. | |
| 5,964,782 A | 10/1999 | Lafontaine et al. | |
| 6,059,719 A | 5/2000 | Yamamoto et al. | |
| 6,086,600 A | 7/2000 | Kortenbach | |
| 6,113,609 A | 9/2000 | Adams | |
| 6,119,913 A | 9/2000 | Adams et al. | |
| 6,159,146 A | 12/2000 | El Gazayerli | |
| 6,174,323 B1 | 1/2001 | Biggs et al. | |
| 6,179,195 B1 | 1/2001 | Adams et al. | |
| 6,197,022 B1 | 3/2001 | Baker | |
| 6,231,561 B1 | 5/2001 | Frazier et al. | |
| 6,245,079 B1 | 6/2001 | Nobles et al. | |
| 6,312,437 B1 | 11/2001 | Kortenbach | |
| 6,358,197 B1 | 3/2002 | Silverman et al. | |
| 6,387,104 B1 | 5/2002 | Pugsley, Jr. | |
| H2037 H | 7/2002 | Yates et al. | |
| 6,494,888 B1 | 12/2002 | Laufer et al. | |
| 6,506,196 B1 | 1/2003 | Laufer | |
| 6,533,796 B1 | 3/2003 | Sauer et al. | |
| 6,537,285 B1 | 3/2003 | Hatasaka, Jr. et al. | |
| 6,540,789 B1 * | 4/2003 | Silverman et al. | 623/23.65 |
| 6,554,845 B1 | 4/2003 | Fleenor et al. | |
| 6,558,400 B2 | 5/2003 | Deem et al. | |
| 6,572,629 B2 | 6/2003 | Kalloo et al. | |
| 6,641,592 B1 | 11/2003 | Sauer et al. | |
| 6,663,639 B1 | 12/2003 | Laufer et al. | |
| 6,695,764 B2 | 2/2004 | Silverman et al. | |
| 6,716,232 B1 | 4/2004 | Vidal et al. | |
| 6,719,763 B2 | 4/2004 | Chung et al. | |
| 6,719,764 B1 | 4/2004 | Gellman et al. | |
| 6,736,828 B1 | 5/2004 | Adams et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,285 B2 | 11/2004 | Laufer et al. | |
| 6,835,199 B2 | 12/2004 | McGuckin, Jr. et al. | |
| 2001/0049509 A1 | 12/2001 | Sekine et al. | |
| 2001/0056282 A1 | 12/2001 | Sonnenschein et al. | |
| 2002/0040226 A1 | 4/2002 | Laufer et al. | |
| 2002/0055757 A1 | 5/2002 | Torre et al. | |
| 2002/0065534 A1 | 5/2002 | Hermann et al. | |
| 2002/0068945 A1 | 6/2002 | Sixto, Jr. et al. | |
| 2002/0072761 A1 | 6/2002 | Abrams et al. | |
| 2002/0078967 A1 | 6/2002 | Sixto, Jr. et al. | |
| 2002/0082621 A1 | 6/2002 | Schurr et al. | |
| 2002/0107530 A1 | 8/2002 | Sauer et al. | |
| 2002/0183768 A1 | 12/2002 | Deem et al. | |
| 2002/0193816 A1 | 12/2002 | Laufer et al. | |
| 2003/0009085 A1 | 1/2003 | Arai et al. | |
| 2003/0055442 A1 | 3/2003 | Laufer et al. | |
| 2003/0065359 A1 | 4/2003 | Weller et al. | |
| 2003/0109892 A1 | 6/2003 | Deem et al. | |
| 2003/0139752 A1 | 7/2003 | Pasricha et al. | |
| 2003/0171651 A1 | 9/2003 | Page et al. | |
| 2003/0171760 A1 | 9/2003 | Gambale | |
| 2003/0176890 A1 | 9/2003 | Buckman et al. | |
| 2003/0181924 A1 | 9/2003 | Yamamoto et al. | |
| 2003/0204205 A1 | 10/2003 | Sauer et al. | |
| 2003/0208209 A1 | 11/2003 | Gambale et al. | |
| 2003/0216613 A1 | 11/2003 | Suzuki et al. | |
| 2003/0225312 A1 | 12/2003 | Suzuki et al. | |
| 2003/0229296 A1 | 12/2003 | Ishikawa et al. | |
| 2003/0236536 A1 | 12/2003 | Grigoryants et al. | |
| 2004/0010271 A1 | 1/2004 | Kortenbach | |
| 2004/0030347 A1 | 2/2004 | Gannoe et al. | |
| 2004/0049095 A1 | 3/2004 | Goto et al. | |
| 2004/0059346 A1 | 3/2004 | Adams et al. | |
| 2004/0082963 A1 | 4/2004 | Gannoe et al. | |
| 2004/0092974 A1 | 5/2004 | Gannoe et al. | |
| 2004/0093091 A1 * | 5/2004 | Gannoe et al. | 623/23.65 |
| 2004/0122452 A1 | 6/2004 | Deem et al. | |
| 2004/0122453 A1 | 6/2004 | Deem et al. | |
| 2004/0122474 A1 | 6/2004 | Gellman et al. | |
| 2004/0138682 A1 | 7/2004 | Onuki et al. | |
| 2004/0147941 A1 | 7/2004 | Takemoto | |
| 2004/0193117 A1 | 9/2004 | Laufer et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215216 A1 | 10/2004 | Gannoe et al. | |
| 2004/0243152 A1 | 12/2004 | Taylor et al. | |
| 2004/0249362 A1 | 12/2004 | Levine et al. | |
| 2004/0249392 A1 | 12/2004 | Mikkaichi et al. | |
| 2004/0249395 A1 | 12/2004 | Mikkaichi et al. | |
| 2005/0033320 A1 | 2/2005 | McGuckin, Jr. et al. | |
| 2005/0033328 A1 | 2/2005 | Laufer et al. | |
| 2005/0080444 A1 * | 4/2005 | Kraemer et al. | 606/192 |
| 2005/0096750 A1 * | 5/2005 | Kagan et al. | 623/23.65 |
| 2005/0216040 A1 | 9/2005 | Gertner et al. | |
| 2005/0216042 A1 | 9/2005 | Gertner | |

FOREIGN PATENT DOCUMENTS

| | | |
|---|---|---|
| FR | 2 768 324 A1 | 3/1999 |
| GB | 2 165 559 A | 4/1986 |
| WO | WO 92/04870 A1 | 4/1992 |
| WO | WO 95/25468 A1 | 9/1995 |
| WO | WO 99/22649 A2 | 5/1999 |
| WO | WO 00/78227 A1 | 12/2000 |
| WO | WO 00/78229 A1 | 12/2000 |
| WO | WO 01/66018 A1 | 9/2001 |

| | | | |
|---|---|---|---|
| WO | WO 01/85034 A1 | 11/2001 |
| WO | WO 01/87144 A1 | 11/2001 |
| WO | WO 01/89370 A2 | 11/2001 |
| WO | WO 01/89393 A1 | 11/2001 |
| WO | WO 02/24080 A2 | 3/2002 |
| WO | WO 02/39880 A2 | 5/2002 |
| WO | WO 02/060328 A1 | 8/2002 |
| WO | WO 02/094105 A2 | 11/2002 |
| WO | WO 03/007796 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/084808 A2 | 10/2004 |
| WO | WO 2004/103189 A1 | 12/2004 |
| WO | WO 2005/004727 A1 | 1/2005 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, (Jul. 1987), pp. 772-776.

Brolin et al., "Experimental Evaluation of Techniques of Gastric Paritioning for Morbid Obesity," *Surgery, Gynecology & Obstetrics*, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, Oct. 1984, pp. 564-568.

* cited by examiner

METHODS FOR PERFORMING GASTROPLASTY

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Field of the Invention

The present invention relates to methods for reducing the effective cross-sectional area of a gastro-intestinal ("GI") lumen.

Extreme or morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, including bypassing an absorptive surface of the small intestine, bypassing a portion of the stomach, and reducing the stomach size, e.g., via Vertical Banded Gastroplasty ("VBG") or Magenstrasse and Mill. These procedures may be difficult to perform in morbidly obese patients and/or may present numerous potentially life-threatening post-operative complications. Thus, less invasive techniques have been pursued.

U.S. Pat. Nos. 4,416,267 and 4,485,805 to Garren et al. and Foster, Jr., respectively, propose disposal of an inflated bag within a patient's stomach to decrease the effective volume of the stomach that is available to store food. Accordingly, the patient is satiated without having to consume a large amount of food. A common problem with these inflated bags is that, since the bags float freely within the patient's stomach, the bags may migrate to, and block, a patient's pyloric opening, the portal leading from the stomach to the duodenum, thereby restricting passage of food to the remainder of the gastrointestinal tract.

Apparatus and methods also are known in which an adjustable elongated gastric band is disposed around the outside of a patient's stomach near the esophagus to form a collar that, when tightened, squeezes the stomach into an hourglass shape, thereby providing a stoma that limits the amount of food that a patient may consume comfortably. An example of an adjustable gastric band is the LAP-BAND® made by INAMED HEALTH of Santa Barbara, Calif.

Numerous disadvantages are associated with using the adjustable gastric band. First, the band may be dislodged if the patient grossly overeats, thereby requiring additional invasive surgery to either reposition or remove the band. Similarly, overeating may cause the band to injure the stomach wall if the stomach over-expands. The laparoscopic disposal of the gastric band around the stomach requires a complex procedure, requires considerable skill on the part of the clinician, and is not free of dangerous complications.

In view of the drawbacks associated with prior art techniques for treating morbid obesity, it would be desirable to provide improved methods for performing gastroplasty.

SUMMARY OF THE INVENTION

Improved methods for performing gastroplasty are achieved by reducing the effective volume or cross-sectional area of the stomach via approximation of gastric tissue. Such reduction preferably is achieved endoluminally, either with or without laparoscopic ports. The methods generally comprise delivering securing elements, such as anchors and/or suture, on opposing sides of the gastric lumen, and then approximating the opposing walls of the lumen via the securing elements. Preferably, serosal-to-serosal folds of gastric tissue are formed on opposing sides of the gastric lumen, and are then approximated. A variety of methods for forming, securing and approximating the opposing serosal-to-serosal folds are described. In one variation, the opposing folds are individually formed and secured, and are then approximated and secured to one another. The individual folds may be reinforced after initial securing. In an alternative variation, the folds are not individually secured, but rather are only secured to one another after approximation. The approximated folds also may be reinforced after initial securing.

In addition to approximation of individual opposing folds of gastric tissue, opposing ridges of serosal-to-serosal folds may be formed and approximated. In this manner, a sleeve or an approximation of significant length may be formed. A variety of methods for forming, securing and approximating the opposing ridges are described.

In one variation, a sleeve, pouch, Magenstrasse, Vertical Banded Gastroplasty ("VBG"), etc. is formed within the stomach by approximating opposing anterior and posterior segments or ridges of the stomach wall at locations inferior to the gastroesophageal junction. In another variation, opposing walls of the stomach are approximated at a plurality of substantially random locations to reduce an effective volume of the stomach. In yet another variation, both a sleeve and random approximations are formed, the random approximations preferably disposed in the larger portion of the stomach excluded by the sleeve. In still another variation, opposing walls of the stomach are approximated over significant lengths at random or specified locations.

DETAILED DESCRIPTION OF THE INVENTION

Figures 1A, 1B, 1C, 1D, 2A, 2C:
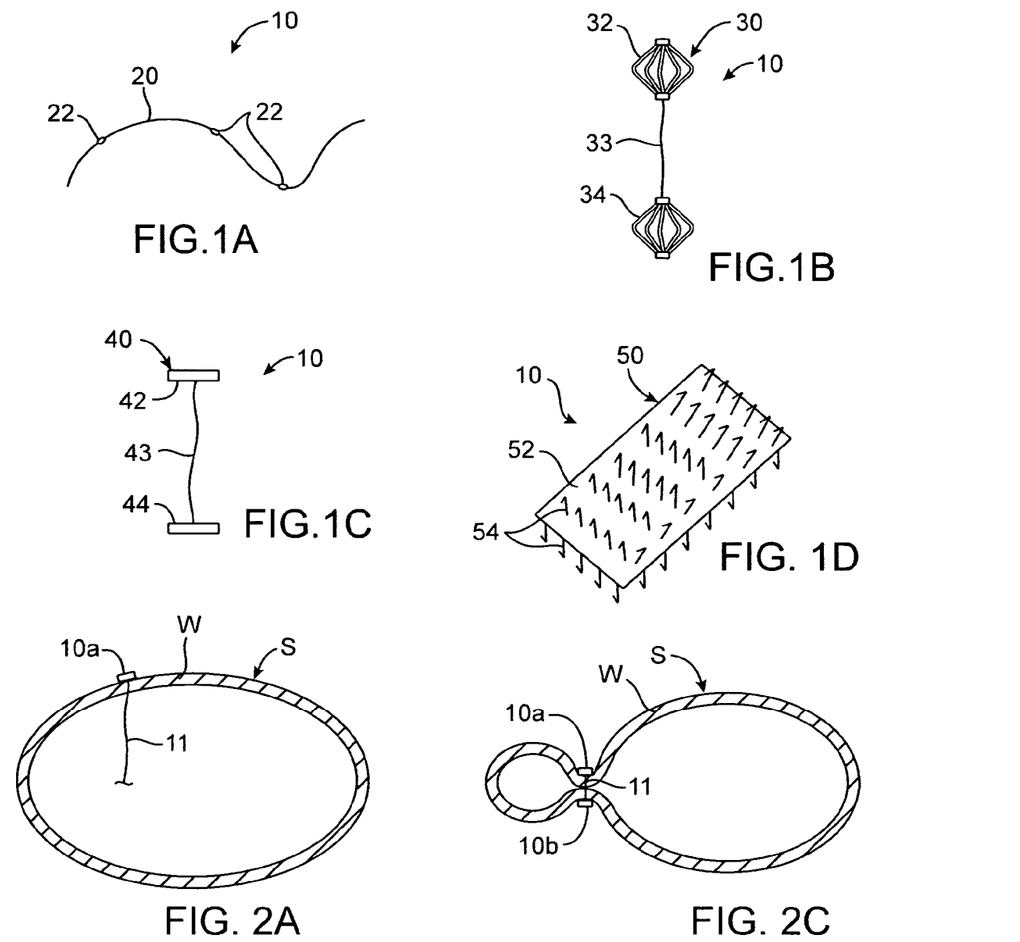
FIGS. 1A-1D are schematic views of illustrative securing elements for use in performing gastroplasty.
FIGS. 2A-2C are schematic cross-sectional views illustrating a method of approximating opposing walls of a patient's gastric lumen.

Improved methods for reducing the effective volume or cross-sectional area of a gastro-intestinal ("GI") lumen via approximation of gastric tissue are described. The methods generally comprise delivering securing elements, such as anchors and/or suture, e.g. knotted suture, on opposing sides of the gastric lumen, and then approximating the opposing walls of the lumen via the securing elements. With reference to FIG. 1, exemplary securing elements for use in performing gastroplasty are described. In FIG. 1A, securing element 10 comprises suture 20 having at least one knot 22. Knots 22 may be pre-tied, or may be tied by the medical practitioner as needed.

In FIG. 1B, securing element 10 comprises anchor assembly 30 having proximal basket 32 and distal basket 34 that are connected by suture 33. The length of suture disposed between the proximal and distal baskets may be fixed or adjustable. Additional exemplary anchor assemblies are described in Applicant's co-pending U.S. patent application Ser. No. 10/612,170, filed Jul. 1, 2003, which is incorporated herein by reference in its entirety.

In FIG. 1C, securing element 10 comprises bar- or t-anchor assembly 40. Assembly 40 comprises proximal t-anchor 42 and distal t-anchor 44 that are connected by suture 43. As with anchor assembly 30, the length of suture disposed between the proximal and distal t-anchors may be fixed or adjustable. Exemplary apparatus and methods for delivering, deploying and adjusting anchor assembly 40 are described in Applicant's co-pending U.S. patent application Ser. No. 10/735, 030, filed Dec. 12, 2003, which is incorporated herein by reference in its entirety.

In FIG. 1D, securing element 10 comprises multi-barbed device 50. Device 50 comprises substrate 52 having a plurality of barbs 54 that project therefrom. Barbs 54 illustratively project from both sides of substrate 52 in FIG. 1D, but it should be understood that the barbs alternatively may project from only one side of the substrate. Barbs 54 optionally may comprise hooks and/or loops, and a plurality of complementary hook/loop multi-barbed devices 50 may be used in conjunction to adhere such complementary devices together. Additional exemplary multi-barbed devices are described in Applicant's co-pending U.S. patent application Ser. No. 09/746,579, filed Dec. 20, 2000, which is incorporated herein by reference in its entirety. Additional variations of securing element 10 will be apparent to those of skill in the art.

Figure 2B:
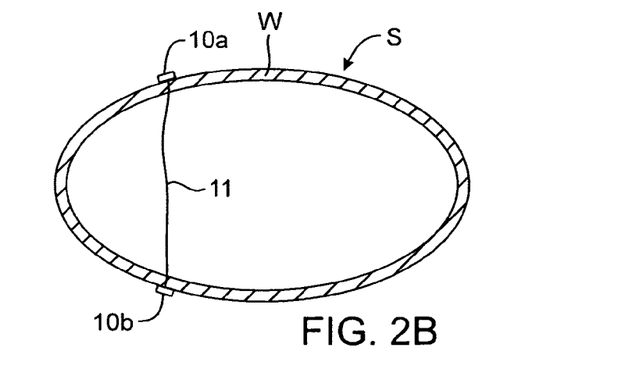

Referring now to FIG. 2, a method of approximating opposing walls of a patient's gastric lumen is described. In FIG. 2A, wall W of stomach S is secured at a first location with securing element 10a. In FIG. 2B, wall W is secured at an opposing second location with securing element 10b. Elements 10a and 10b are connected by suture 11. In FIG. 2C, the length of suture disposed between elements 10a and 10b is reduced, thereby approximating the opposing locations of the stomach wall.

Prior art gastroplasty techniques typically achieve gastroplasty by manipulating or operating on the exterior of a patient's stomach. However, in order to minimize invasiveness, it is desirable to endoluminally perform gastroplasty, for example, via instruments inserted down a patient's throat or via instruments inserted laparoscopically and transgastrically within the gastric lumen. Although tissue approximation may be achieved endoluminally utilizing the method of FIG. 2, securing elements 10 extend from the interior of stomach S to the exterior of the stomach. This may be undesirable for some high-risk patients or procedures, as a possibility exists of puncturing or otherwise damaging surrounding anatomy when placing securing elements across gastric wall W to the exterior of the gastric lumen.

Figure 3:
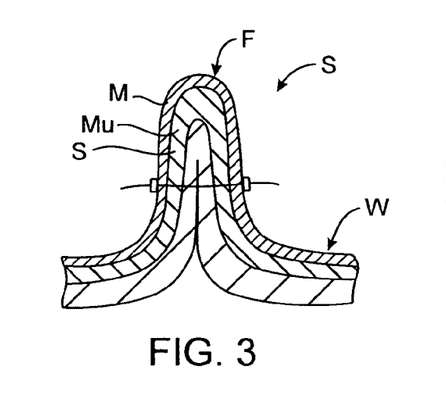
FIG. 3 is a schematic side-sectional view illustrating formation and securing of a serosal-to-serosal fold.

With reference to FIG. 3, a method for endoluminally securing the wall at specified locations without exiting the gastric lumen is described. Gastric wall W of stomach S comprises multiple tissue layers, including mucosa M, muscularis Mu and serosa S. In FIG. 3, wall W has been plicated to form serosal-to-serosal tissue fold F. Exemplary methods and apparatus for plicating tissue wall W to form fold F are described, for example, in Applicant's co-pending U.S. patent application Ser. No. 10/735,030, filed Dec. 12, 2003, which previously has been incorporated herein by reference in its entirety. Tissue fold F has been secured with securing element 10 illustratively having a first portion disposed on a first side of fold F, a suture that extends through the fold, and a second portion disposed on the opposite side of fold F. The length of suture disposed between the first and second portions of securing element 10 preferably is adjustable to provide specified tensioning across fold F.

Referring now to FIG. 4, a method of forming, securing and approximating opposing serosal-to-serosal folds is described. In FIG. 4A, a first serosal-to-serosal fold $F_1$ is formed and is secured at a first location within stomach S via first securing element 10a. Likewise, a second serosal-to-serosal fold $F_2$ is formed and secured at a second opposing location within stomach S via second securing element 10b. A first portion of securing element 10c then is passed through first fold $F_1$, while a second portion of the securing element is passed through second fold $F_2$, as in FIG. 4B. In FIG. 4C, the length of suture disposed between the first and second portions of securing element 10c is reduced, thereby approximating opposing tissue folds $F_1$ and $F_2$. As will apparent to those of skill in the art, such approximation may be used to achieve endoluminal gastroplasty.

Figure 4A:
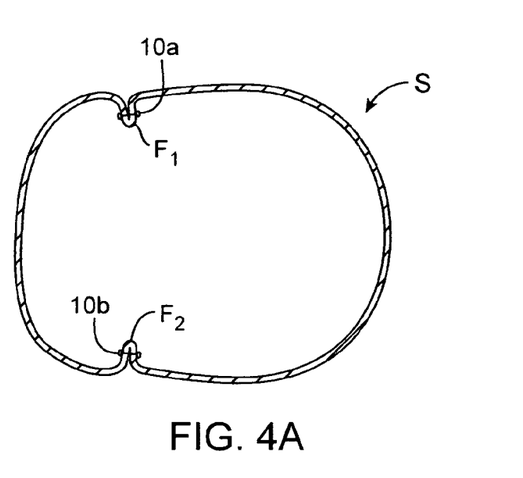
FIGS. 4A-4D are schematic cross-sectional views illustrating a method of forming, securing and approximating opposing serosal-to-serosal folds, as well as optionally reinforcing the individual folds.
Figure 4B:
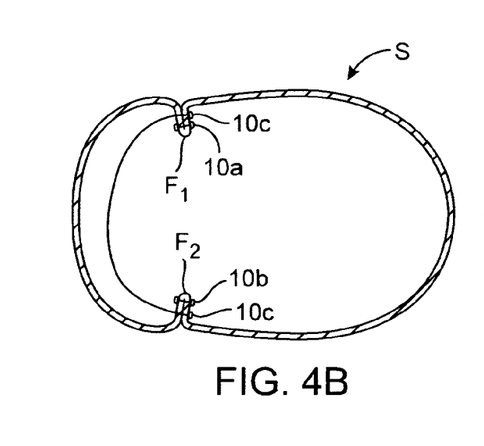
Figure 4C:
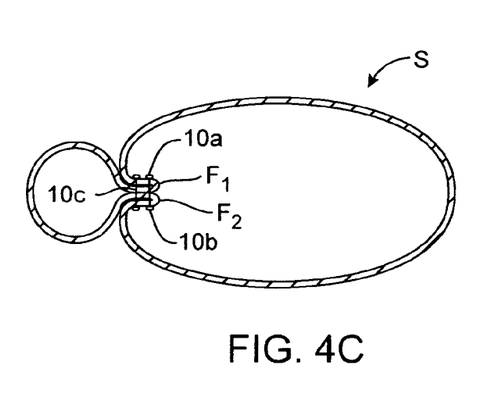
Figure 4D:
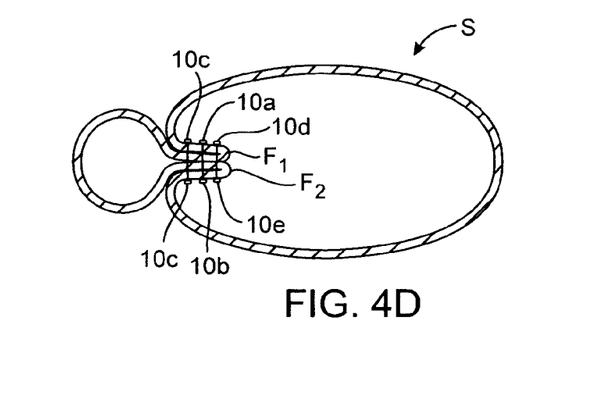

The serosal-to-serosal tissue folds optionally may be reinforced to enhance long-term durability. In FIG. 4D, an additional securing element has been placed through each serosal-to-serosal fold. Securing element 10d has been placed through fold $F_1$, while securing element 10e has been placed through fold $F_2$. Although folds $F_1$ and $F_2$ illustratively have been reinforced after they have been approximated, it will be apparent to those of skill in the art that the folds alternatively may be reinforced prior to, or during, approximation.

Figure 5:
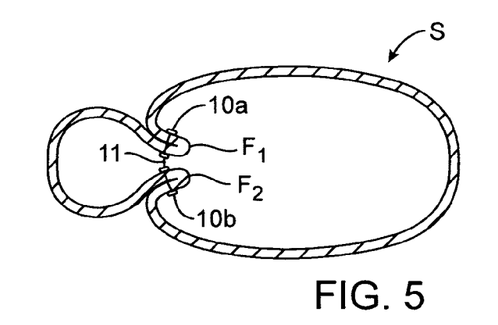
FIG. 5 is a schematic cross-sectional view illustrating an alternative method of forming, securing and approximating opposing serosal-to-serosal folds.

With reference to FIG. 5, an alternative method of forming, securing and approximating opposing serosal-to-serosal folds is described. In FIG. 5, first securing element 10a, which secures tissue fold $F_1$, and second securing element 10b, which secures tissue fold $F_2$, are connected to one another by suture 11. Tissue folds $F_1$ and $F_2$ are approximated by reducing the length of suture 11 disposed between securing elements 10a and 10b (in FIG. 5, the folds illustratively are shown in a partially approximated configuration).

Figure 6A:
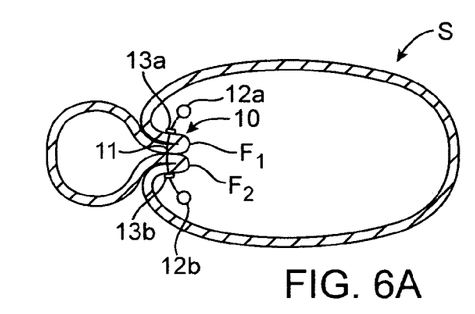
FIGS. 6A and 6B are schematic cross-sectional views illustrating another alternative method of forming, securing and approximating the folds, as well as optionally reinforcing the approximated folds.

Referring now to FIG. 6, another alternative method of forming, securing and approximating opposing tissue folds is described. In FIG. 6A, a single securing element 10 is used to form and secure both first tissue fold $F_1$ and second tissue fold $F_2$, as well as to approximate the two tissue folds. Securing element 10 preferably also is configured to maintain such approximation of the tissue folds.

Securing element 10 illustratively comprises first and second suture loops 12a and 12b that may be grasped to adjust the length of suture disposed between the first and second tissue folds to approximate the folds. For example, one or both of suture loops 12a and 12b may be pulled away from the tissue folds while one or both of anchoring elements 13a and 13b of securing element 10 are held stationary or advanced toward the folds. Alternatively, the suture loop(s) may be held stationary while the anchoring element(s) are advanced. The anchoring elements preferably comprise a ratcheting mechanism that adjusts, e.g. reduces, and maintains the length of suture 11 disposed between the anchoring elements (thereby approximating the tissue folds) upon such force application. Illustrative ratcheting mechanisms for securing element 10 are described, for example, in Applicant's co-pending U.S. patent application Ser. No. 10/735,030, filed Dec. 12, 2003, which previously has been incorporated herein by reference.

Figure 6B:
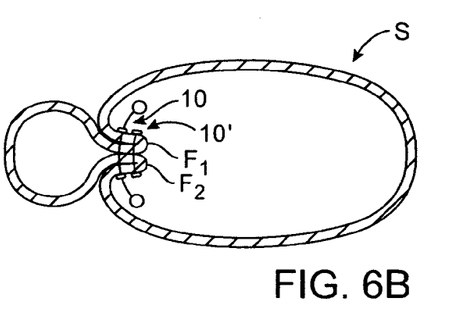

As seen in FIG. 6B, the approximated serosal-to-serosal tissue folds may be reinforced to ensure that the folds remain closely approximated. In FIG. 6B, securing element 10' has been placed across folds $F_1$ and $F_2$ after the folds have been approximated. Element 10' alternatively may be placed prior to approximation, e.g., to better distribute forces during approximation.

Figure 7:
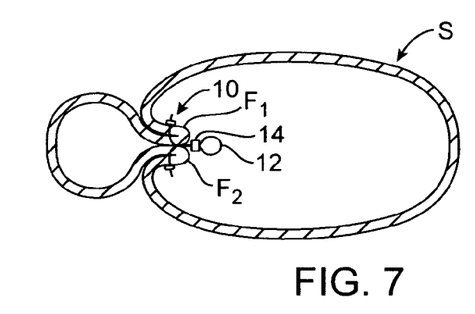
FIG. 7 is a schematic cross-sectional view illustrating yet another alternative method of forming, securing and approximating the folds.

With reference to FIG. 7, yet another alternative method for approximating tissue folds is described. As with the method of FIG. 6A, in FIG. 7 the tissue folds are formed and approximated with a single securing element 10. However, the securing element only comprises a single suture loop 12 (illustratively in combination with optional cinching or crimping element 14), which is disposed between tissue folds $F_1$ and $F_2$. In this manner, ratcheting of securing element 10 to approximate folds $F_1$ and $F_2$ may be achieved by grasping suture loop 12 between the folds.

Figure 8:
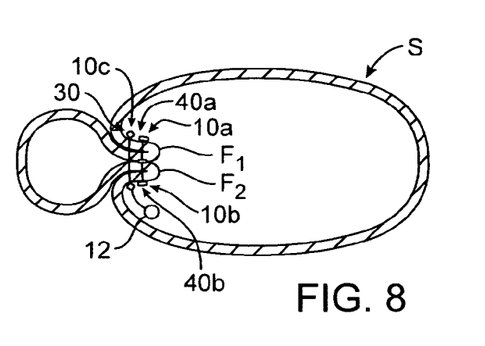
FIG. 8 is a schematic cross-sectional view illustrating still another method of forming, securing and approximating the folds.

FIG. 8 illustrates still another alternative method. Tissue folds $F_1$ and $F_2$ are formed and secured with first and second securing elements 10a and 10b, illustratively comprising previously described t-anchor assemblies 40a and 40b. The folds are approximated via securing element 10c, which illustratively comprises previously described anchor assembly 30. As in FIG. 7, securing element 10c comprises only a single suture loop 12; however, the loop illustratively is disposed on the outer side of tissue fold $F_2$, as opposed to between tissue folds $F_1$ and $F_2$.

Figure 9A:
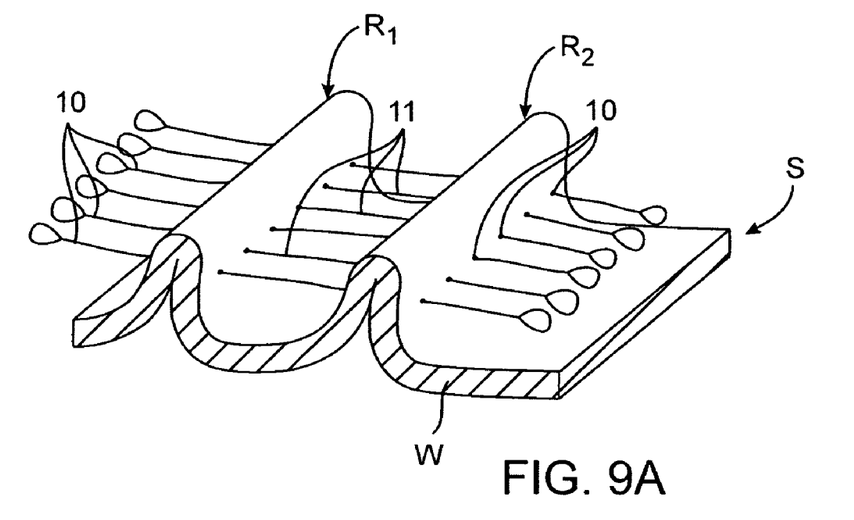
FIGS. 9A and 9B are schematic side-sectional views illustrating a method of forming, securing and approximating opposing ridges of serosal-to-serosal gastric tissue folds.
Figure 9B:
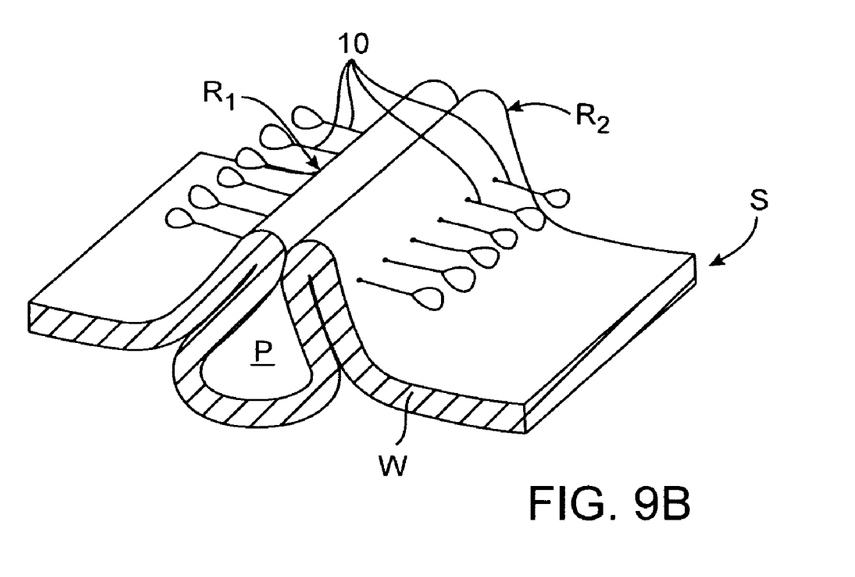

Referring now to FIG. 9, in addition to forming, securing and approximating opposing serosal-to-serosal gastric tissue folds, opposing ridges of such folds may be formed, secured, approximated, etc. In FIG. 9, first ridge $R_1$ and opposing second ridge $R_2$ of serosal-to-serosal tissue fold are formed, secured and approximated, illustratively utilizing a variation of the method described hereinabove with respect to FIG. 6.

As will be apparent to those of skill in the art, although ridges $R_1$ and $R_2$ illustratively are formed and approximated utilizing a method adapted from that described with respect to FIG. 6, any alternative method, including any adaptation of the methods described with respect to FIGS. 4, 5, 7 and/or 8, may additionally or alternatively be utilized.

As seen in FIG. 9A, a plurality of securing elements 10 have been placed across ridges $R_1$ and $R_2$, with sutures 11 extending between the ridges. In FIG. 9B, the length of sutures 11 between the ridges has been reduced in order to approximate the ridges, thereby forming an approximation of significant length and/or a sleeve or pouch P within stomach S. Pouch P optionally may be reinforced, e.g. via additional securing elements or via suture wrapped in a circular manner about the apexes of approximated ridges $R_1$ and $R_2$. Additionally or alternatively, a stabilizing agent, e.g. fibrin, may be injected into the ridges to secure and/or reinforce the ridges, for example, by coagulating blood within the ridges.

Figure 10A:
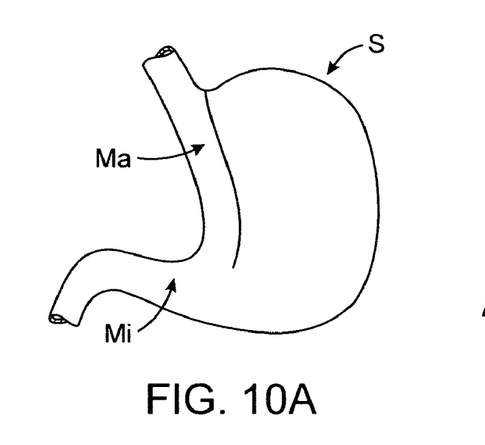
FIGS. 10A and 10B are side and side-sectional views illustrating a method of approximating anterior and posterior segments or ridges of a patient's stomach to form a sleeve, Magenstrasse and Mill, VBG pouch, etc.
Figure 10B:
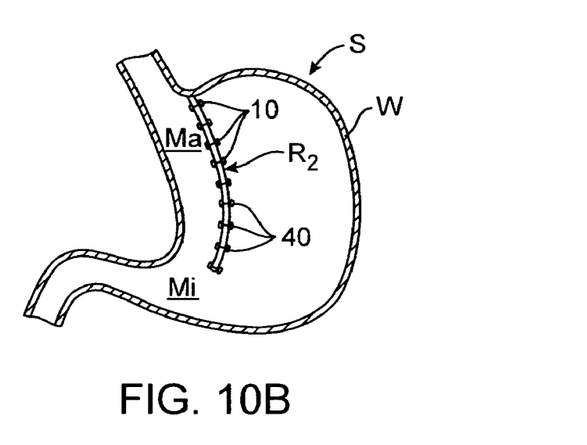

Referring now to FIG. 10 in conjunction with FIG. 9, when sleeve or pouch P is formed within a patient's stomach from opposing anterior and posterior segments or ridges of the stomach wall W at locations just inferior to the patient's gastroesophageal junction GEJ, the pouch forms an endoluminal VBG or Magenstrasse and Mill (dependent upon the profile, diameter, length, etc., of the pouch). In FIG. 10A, an external side view of stomach S illustrates formation of a Magenstrasse Ma and Mill Mi gastroplasty within the stomach. FIG. 10B illustrates the same via a side-sectional view showing posterior ridge $R_2$ formed with securing elements 10, illustratively t-anchor assemblies 40 of FIG. 1C.

As will apparent to those of skill in the art, endoluminal pouch or Magenstrasse gastroplasty optionally may be achieved without forming tissue fold ridges $R_1$ and $R_2$. For example, the opposing walls of stomach S may be approximated to form Magenstrasse Ma in a manner similar to that described hereinabove with respect to FIG. 2, i.e. via securing elements that exit the gastric lumen. Formation of Magenstrasse Ma reduces the effective volume and/or cross-sectional area of stomach S by excluding the fundus and a portion of the body of the stomach from food, while still allowing fluid to flow from the excluded region to antril mill Mi.

Figure 11A:
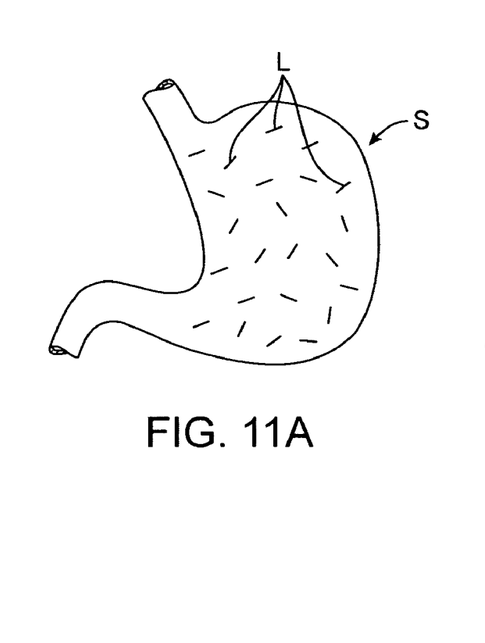
FIGS. 11A and 11B are side and side-sectional views illustrating a method of approximating opposing sides of the gastric lumen at substantially random locations.

Referring now to FIG. 11, an alternative method for performing gastroplasty is described. As seen in FIG. 11A, opposing sides of stomach S may be approximated and secured at substantially random locations L. It is expected that such random approximations will reduce the effective volume and/or cross-sectional area of the stomach and produce a sensation of satiety by increasing the resident time of food within the stomach. Furthermore, it is expected that the approximations will reduce a quantity of food that a patient may comfortably consume at one sitting and/or may reduce peristalsis of the stomach.

Figure 11B:
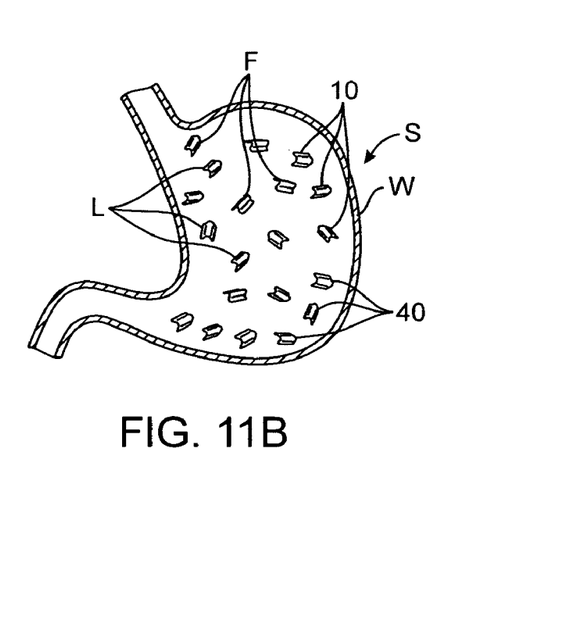

The side-sectional view of FIG. 11B shows illustrative posterior folds F formed with securing elements 10 illustratively comprising t-anchor assemblies 40 of FIG. 1C. Such folds may be approximated with complementary opposing anterior folds to form the approximations of FIG. 11A at substantially random locations L. In order to achieve a desired degree of weight loss, a medical practitioner may specify the aggressiveness (i.e. the volume and/or density) of random approximation formation. Furthermore, as an alternative to random location selection, approximations may be made at specified locations within stomach S to provide the patient's gastric lumen with any specified/desired geometry.

Figure 12A:
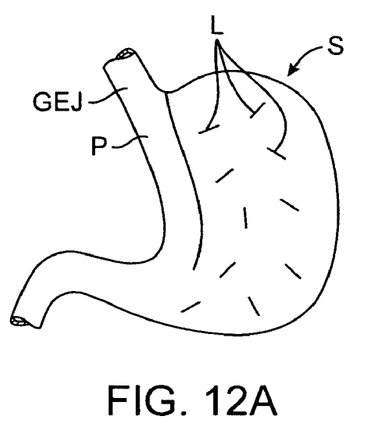
FIGS. 12A and 12B are side and side-sectional views illustrating a method of forming both a sleeve and random approximations within the gastric lumen.
Figure 12B:
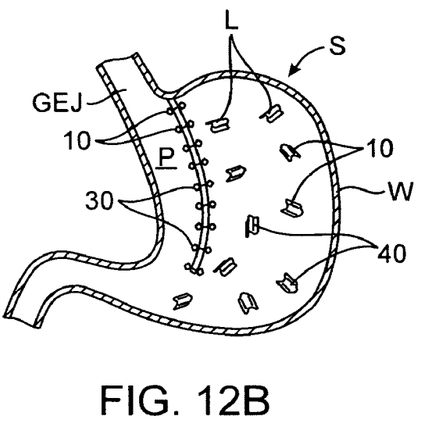

With reference to FIG. 12, a method of forming both a sleeve and random approximations within the gastric lumen is described. Formation of pouch P has been described previously hereinabove with respect to FIGS. 9 and 10, while formation of approximations at random locations L has been described with respect to FIG. 11. As seen in FIG. 12A, sleeve or pouch P may extend inferior to the patient's gastroesophageal junction GEJ, while approximations are disposed at substantially random locations L within stomach S. As seen in FIG. 12B, pouch P illustratively has been formed with securing elements 10 comprising anchor assemblies 30 of FIG. 1B, while the random approximations illustratively have been formed with securing elements comprising t-anchor assemblies 40 of FIG. 1C.

Pouch P and the approximations at random locations L may be formed concurrently or successively in any order. Random locations L preferably are confined to the region of stomach S disposed outside of sleeve or pouch P to ensure safe passage of food through the pouch. Providing pouch P in conjunction with approximations at random locations L may more fully restrict the stomach, thereby enhancing a sensation of satiety, prolonging the resident time of food within the stomach, and/or reducing a quantity of food that may be comfortably consumed.

Figure 13A:
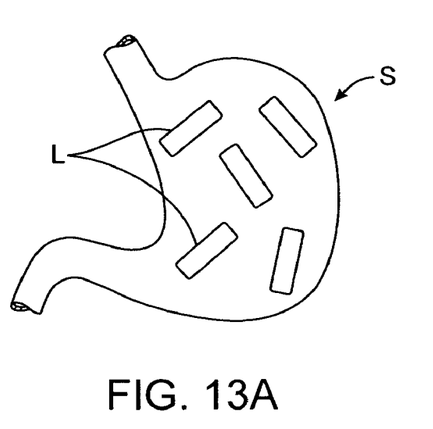
FIGS. 13A and 13B are side and side-sectional views illustrating a method of approximating opposing walls of the stomach over significant lengths.
Figure 13B:
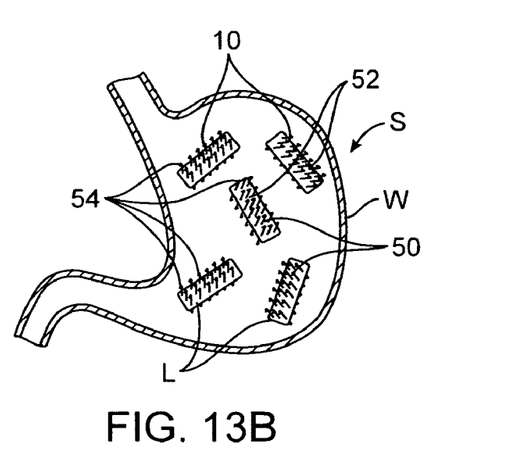

Referring now to FIG. 13, a method of approximating opposing walls of the stomach over significant length(s) at random or specified locations is described. As seen in FIG. 13A, stomach S illustratively has been approximated at multiple random or specified locations L over significant lengths, for example, lengths preferably greater than or equal to about 1 cm, and even more preferably greater than or equal to about 2 cm. As seen in FIG. 13B, such approximations have been achieved by utilizing securing elements 10 comprising multi-barbed devices 50 of FIG. 1D. For example, barbs 54 extending from first surfaces of substrates 52 of devices 50 may be adhered to a first wall of stomach S, while barbs 54 extending from opposing second surfaces of the substrates may be adhered to opposing walls of the stomach, thereby approximating and securing the opposing walls. The lengths of devices 50 may be specified as desired. Additional and/or alternative methods for approximating opposing walls of the stomach over significant lengths will be apparent to those of skill in the art.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A method for performing gastroplasty, the method comprising:
    inserting a securing element down the throat of a patient to a position within the stomach of the patient;
    forming tissue folds on opposing walls of a patient's stomach;
    approximating the tissue folds;
    securing the approximated tissue folds with the securing element; and
    reinforcing the approximated and secured tissue folds.

2. The method of claim 1, wherein approximating the tissue folds further comprises approximating the tissue folds with instruments advanced down the patient's throat.

3. The method of claim 1, wherein forming tissue folds further comprises forming serosal-to-serosal tissue folds.

4. The method of claim 1, wherein securing the approximated tissue folds comprises securing the tissue folds with at least one securing element, and wherein approximating the tissue folds further comprises approximating the tissue folds via a ratcheting or tensioning mechanism of the securing element.

5. A method for performing gastroplasty, the method comprising:
    endoluminally forming a plurality of tissue folds secured by tissue anchors on opposing walls of a patient's stomach with instruments advanced down the throat of the patient:
    endoluminally approximating the opposing walls with instruments advanced down the throat of the patient; and
    reinforcing the approximated opposing walls using a plurality of tissue anchors.

* * * * *